United States Patent [19]

Uustalu

[11] Patent Number: 4,552,817
[45] Date of Patent: Nov. 12, 1985

[54] INACTIVATED POLYURETHANE AND A METHOD FOR PREPARING IT

[75] Inventor: Jaan M. Uustalu, Lund, Sweden

[73] Assignee: Protector Agentur AB, Malmo, Sweden

[21] Appl. No.: 574,028

[22] PCT Filed: Apr. 28, 1983

[86] PCT No.: PCT/SE83/00169
§ 371 Date: Dec. 29, 1983
§ 102(e) Date: Dec. 29, 1983

[87] PCT Pub. No.: WO83/03837
PCT Pub. Date: Nov. 10, 1983

[30] Foreign Application Priority Data

May 4, 1982 [SE] Sweden ............................... 8202776

[51] Int. Cl.$^4$ ............................................. B32B 27/08
[52] U.S. Cl. .................................. 428/423.7; 264/129; 264/255; 428/424.2; 428/424.4
[58] Field of Search ................... 264/46.6, 255, 129, 264/45.1; 428/423.7, 424.2, 424.4

[56] References Cited

U.S. PATENT DOCUMENTS

| | | | |
|---|---|---|---|
| 4,018,948 | 4/1977 | Saracsan et al. | 427/316 |
| 4,242,410 | 12/1980 | König et al. | 264/255 X |
| 4,282,285 | 8/1981 | Mohiuddin | 264/46.6 X |
| 4,294,880 | 10/1981 | Nishida | 264/46.6 X |
| 4,331,735 | 5/1982 | Shanoski | 264/255 X |
| 4,389,454 | 6/1983 | Horacek et al. | 264/46.6 X |
| 4,487,808 | 12/1984 | Lambert | 428/424.2 X |

FOREIGN PATENT DOCUMENTS

| | | |
|---|---|---|
| 6308 | 1/1980 | European Pat. Off. . |
| 2633743 | 3/1977 | Fed. Rep. of Germany . |
| 3124982 | 2/1982 | Fed. Rep. of Germany . |

*Primary Examiner*—Philip Anderson
*Attorney, Agent, or Firm*—Kokjer, Kircher, Bradley, Wharton, Bowman & Johnson

[57] ABSTRACT

Inactivated polyurethane and a method for preparing it are disclosed. The polyurethane is inactivated by being coated with a layer of a polymer which contains e.g. hydroxyl groups. These hydroxyl groups react with free isocyanate molecules in the polyurethane material and a chemical bonding occurs which prevents noxious isocyanate molecules from coming into contact with the ambient atmosphere. The inactivated polyurethane will thereby be useful in products where it comes into direct contact with the skin or the mucous membranes.

4 Claims, No Drawings

INACTIVATED POLYURETHANE AND A METHOD FOR PREPARING IT

The present invention relates to an inactivated polyurethane and a method for preparing it.

Polyurethane (PUR) is generally manufactured by a reaction between polyfunctional isocyanates and alcohols. The finished product then has a certain residual isocyanate content. It has long been known that isocyanate molecules are toxic, this having restricted the use of polyurethane to fields where a certain isocyanate content has not been considered harmful.

An indication of the toxicity of isocyanate is that the hygienic limit value for its presence in the atmosphere (for instance in a workshop) is at present (in Sweden) as low as 0.01 ppm [ml (gas)/$m^2$ (air)]. However, there is no limit value for the residual content of isocyanate monomers in completely cured polyurethane material, which may be attributable to the fact that no suitable method of analysis for detecting so low contents of isocyanate molecules as here contemplated has been elaborated.

The commonest symptom of exposure to isocyanate are allergic troubles in the form of irritations of the mucous membranes and the skin. Since the residual isocyanate monomer content of completely cured polyurethane is very low, it is possible nevertheless in many instances to use polyurethane in cases where the human body comes into contact with the material, if an air gap can be provided between the polyurethane and the body. One example of this is the use as padding in mattresses which are covered with a fabric.

Considering the other properties of polyurethane, it would also serve well in other products, but its use has hitherto been hampered to a great extent by its noxiousness to the skin and the mucous membranes.

The object of the present invention therefore is to provide an inactivated polyurethane which can also be used in such products as will come into direct contact with the skin, such as ear protectors or dressing materials, e.g. plaster.

This object is achieved by coating polyurethane with a layer of a polymer which contains functional groups capable of reacting with isocyanate. Free isocyanate groups leaving the polyurethane material will then be prevented not only mechanically from escaping out into the ambient atmosphere but will react with the alcohol groups in the polymer layer and be chemically bound therein.

Examples of preferred functional groups which are capable of reacting with isocyanate are hydroxyl groups.

The coating of the polyurethane can be carried out in various ways. Thus, the polyurethane can first be molded to the desired shape and thereafter be coated with a thin layer of a suitable polymer which then reacts with isocyanate groups in the polyurethane.

Another mode of producing the coating is first to apply a thin layer of a suitable polymer to the inner side of the mold in which the polyurethane is to be shaped, and then form the polyurethane in the mold. Functional groups in the polymer will then react with isocyanate groups in the polyurethane, whereby the layer of polymer is chemically bonded to the polyurethane.

A suitable hydroxyl group containing polymer is e.g. polyvinyl alcohol, but other hydroxyl group containing polymers may also be used, such as partly hydrolyzed polyvinyl acetate or copolymers containing vinyl alcohol or hydrolyzed polyvinyl acetate, polymers prepared from vinyl and acrylate monomers containing hydroxyl groups, or hydroxyl group-terminated low molecular polyesters.

For a more detailed illustration of the invention, reference is now had to the following Example which is however not meant in any way to restrict the scope of the present invention.

EXAMPLE

Since the isocyanate content of polyurethane is so low that it cannot be analyzed by conventional methods, a model test has been conducted in order to illustrate the penetration of the isocyanate molecule through polyvinyl alcohol.

A mixture of toluene-2,4-diisocyanate (2,4-TDI) and toluene-2,6-diisocyanate (2,6-TDI), which are common starting materials for the preparation of polyurethane, was batched in a test tube over which the sheeting to be examined was stretched. Over the sheeting was placed a sealing flask having two taps. The polymer sheeting and the TDI were heated to 65°–70° C. 20 l of air were blown for 20 min. through one tap of the flask and were collected at the other tap. The amount of isocyanate which had penetrated through the sheeting and been entrained by the current of air was determined by a gas chromatographic standard method.

Tests were performed with sheetings of polyethylene, polyvinyl alcohol and polyvinyl alcohol treated with a catalyst (DABCO 33 LV). The catalyst used is of the type employed in the production of polyurethane, and residues of spent catalyst are always present in the finished material.

It was found that the amount of isocyanate that had penetrated through the sheeting of polyvinyl alcohol (not treated by catalyst) was about 50 times less than the amount that had penetrated through the polyethylene sheeting. The permeability of the catalyst-treated polyvinyl alcohol sheeting to isocyanate molecules was still less.

A lesser amount of 2,4-TDI than of 2,6-TDI initially penetrates through the polyvinyl alcohol sheeting. Since 2,4-TDI is far more reactive than 2,6-TDI, this is indicative of a reaction taking place between the isocyanate molucules and the alcohol groups. The more reactive molecule is thus barred to a greater extent by the reactive protective film.

I claim:

1. An article of manufacture for use by a person and comprising an inactivated polyurethane article coated with a protective layer to prevent migration of free isocyanate from the polyurethane, said protective layer characterised by a hydroxyl group containing polymer the hydroxyl groups of which are capable of reacting with free isocyanate groups in the polyurethane, said polymer comprising a member of the group polyvinyl alcohol, partly hydrolyzed polyvinyl acetate, copolymers of vinyl alcohol and hydrolyzed polyvinyl acetate, the product of polymerization of hydroxyl containing vinyl monomers, the product of polymerization of hydroxyl containing acrylate monomers, and hydroxyl group-terminated low molecular polyesters.

2. A method for preparing an article of manufacture to be used by a person and comprising an inactivated polyurethane, said method coating the polyurethane with a protective layer of a hydroxyl group containing polymer the hydroxyl groups of which are capable of reacting with free isocyanate groups in the polyurethane thereby protecting the person from the isocyanate, said polymer comprising a member of the group polyvinyl alcohol, partly hydrolyzed polyvinyl acetate, copolymers of vinyl alcohol and hydrolyzed polyvinyl acetate, the product of polymerization of hydroxyl containing vinyl monomers, the product of polymerization of hydroxyl containing acrylate monomers, and hydroxyl group-terminated low molecular polyesters.

3. Method as claimed in claim 2, characterised in that said protective layer is effected by coating the polyurethane with the protective layer after molding the polyurethane to a desired shape.

4. Method as claimed in claim 2, characterised in that said protective layer is effected by applying a layer of the polymer to the inner side of a mold in which the polyurethane is to be shaped, and thereafter molding the polyurethane.

* * * * *